United States Patent
Kreutzer et al.

(10) Patent No.: US 6,746,855 B2
(45) Date of Patent: Jun. 8, 2004

(54) L-LYSINE-PRODUCING CORYNEBACTERIA AND PROCESS FOR THE PREPARATION OF L-LYSINE

(75) Inventors: Caroline Kreutzer, Melle (DE); Stephan Hans, Osnabruck (DE); Mechthild Rieping, Bielefeld (DE); Bettina Mockel, Bielefeld (DE); Walter Pfefferle, Halle (DE); Lothar Eggeling, Julich (DE); Hermann Sahm, Julich (DE); Miroslav Patek, Prague (CZ)

(73) Assignees: Dégussa-Hüls Aktiengesellschaft, Frankfurt am Main (DE); Forschungszentrum Jülich GmbH, Jülich (DE)

( * ) Notice: Subject to any disclaimer, the term of this patent is extended or adjusted under 35 U.S.C. 154(b) by 0 days.

(21) Appl. No.: 10/337,985

(22) Filed: Jan. 8, 2003

(65) Prior Publication Data

US 2003/0162269 A1 Aug. 28, 2003

Related U.S. Application Data

(63) Continuation of application No. 09/801,321, filed on Mar. 8, 2001, now abandoned, which is a continuation-in-part of application No. 09/353,133, filed on Jul. 14, 1999, now Pat. No. 6,200,785.

(30) Foreign Application Priority Data

Jul. 7, 1999 (DE) .......................... 199 31 317

(51) Int. Cl.⁷ .............................. C12P 13/08

(52) U.S. Cl. ................ 435/115; 435/252.32; 435/320.1
(58) Field of Search ........................... 435/115, 252.32, 435/320.1

(56) References Cited

U.S. PATENT DOCUMENTS 6,200,785 B1 * 3/2001 Kreutzer et al. ............ 435/115
2003/0049804 A1    3/2003 Pompejus et al.

FOREIGN PATENT DOCUMENTS

| DE | 19548222 | 6/1997 |
|----|----------|--------|
| DE | 19831609 | 4/1999 |
| EP | 435132 | 7/1991 |
| EP | 854189 | 7/1998 |
| EP | 1 108 790 | 6/2001 |
| WO | WO 01 00 843 | 1/2001 |

OTHER PUBLICATIONS

EMBL database Acc. No. X67737, Apr. 1993.
Hungarian Search Report P0002585 dated Jun. 27, 2002.

* cited by examiner

*Primary Examiner*—James Ketter
(74) *Attorney, Agent, or Firm*—Pillsbury Winthrop LLP (57) ABSTRACT

The invention relates to L-lysine-producing strains of corynebacteria with enhanced lysE gene (lysine export carrier gene), in which strains additional genes chosen from the group comprising the dapA gene (dihydrodipicolinate synthase gene), the lysC gene (aspartate kinase gene), the dapB gene (dihydrodipicolinate reductase gene) and the pyc gene, but especially the dapA gene and the lysC gene (aspartate kinase gene), are enhanced and, in particular, overexpressed, and to a process for the preparation of L-lysine.

1 Claim, 3 Drawing Sheets

Figure 1: Plasmid pEC7lysE

Figure 2: Plasmid pEC7dapB

Figure 3: Plasmid pEC7dapBlysE

L-LYSINE-PRODUCING CORYNEBACTERIA AND PROCESS FOR THE PREPARATION OF L-LYSINE

This is a continuation of U.S. patent application Ser. No. 09/801,321, filed Mar. 8, 2001, now abandoned, which is a continuation-in-part of U.S. patent application Ser. No. 09/353,133, filed Jul. 14, 1999, now U.S. Pat. No. 6,200,785, issued on Mar. 13, 1999, which claims priority to German Patent Appl. No. 199 31 317.2, flied Jul. 7, 1999.

The invention relates to L-lysine-producing strains of corynebacteria with enhanced lysE gene (lysine export carrier gene), in which strains additional genes, chosen from the group comprising the dapA gene (dihydrodipicolinate synthase gene), the lysC gene (aspartate kinase gene), the dapB gene (dihydrodipicolinate reductase gene) and the pyc gene, but especially the dapA gene and the lysC gene (aspartate kinase gene), are amplified and, in particular, overexpressed, and to a process for the preparation of L-lysine.

STATE OF THE ART

L-Lysine is a commercially important L-amino acid which is used especially as a feed additive in animal nutrition. The need has been steadily increasing in recent years.

L-Lysine is prepared by a fermentation process with L-lysine-producing strains of corynebacteria, especially *Corynebacterium glutamicum*. Because of the great importance of this product, attempts are constantly being made to improve the preparative process. Improvements to the process may relate to measures involving the fermentation technology, e.g. stirring and oxygen supply, or the composition of the nutrient media, e.g. the sugar concentration during fermentation, or the work-up to the product form, e.g. by ion exchange chromatography, or the intrinsic productivity characteristics of the microorganism itself.

The productivity characteristics of these microorganisms are improved by using methods of mutagenesis, selection and mutant choice to give strains which are resistant to antimetabolites, e.g. S-(2-aminoethyl)cysteine, or auxotrophic for amino acids, e.g. L-leucine, and produce L-lysine.

Methods of recombinant DNA technology have also been used for some years in order to improve L-lysine-producing strains of *Corynebacterium glutamicum* by amplifying individual biosynthesis genes and studying the effect on L-lysine production.

Thus, EP-A-0 088 166 reports the increase in productivity, after amplification, of a DNA fragment conferring resistance to aminoethylcysteine. EP-B-0 387 527 reports the increase in productivity, after amplification, of an lysC allele coding for a feedback-resistant aspartate kinase. EP-B-0 197 335 reports the increase in productivity, after amplification, of the dapA gene coding for dihydrodipicolinate synthase. EP-A-0 219 027 reports the increase in productivity, after amplification, of the asd gene coding for aspartate semialdehyde dehydrogenase. Pisabarro et al. (Journal of Bacteriology 175(9), 2743–2749 (1993)) describe the dapB gene coding for dihydrodipicolinate reductase.

The effect of the amplification of primary metabolism genes on L-lysine production has also been studied. Thus EP-A-0 219 027 reports the increase in productivity, after amplification, of the aspC gene coding for aspartate aminotransferase. EP-B-0 143 195 and EP-B-0 358 940 report the increase in productivity, after amplification, of the ppc gene coding for phosphoenolpyruvate carboxylase. DE-A-198 31 609 reports the increase in productivity, after amplification, of the pyc gene coding for pyruvate carboxylase.

Finally, DE-A-195 48 222 describes that an increased activity of the L-lysine export carrier coded for by the lysE gene promotes lysine production.

In addition to these attempts to amplify an individual gene, attempts have also been made to amplify two or more genes simultaneously and thereby to improve L-lysine production in corynebacteria. Thus, DE-A-38 23 451 reports the increase in productivity, after simultaneous amplification, of the asd gene and the dapA gene from *Escherichia coli*. DE-A-39 43 117 discloses the increase in productivity, after simultaneous amplification, of an lysC allele coding for a feedback-resistant aspartate kinase and of the dapA gene by means of plasmid pJC50. EP-A-0 841 395 particularly reports the increase in productivity, after simultaneous amplification, of an lysC allele coding for a feedback-resistant aspartate kinase and of the dapB gene; further improvements could be achieved by additional amplification of the dapB, lysA and ddh genes. EP-A-0 854 189 describes the increase in productivity, after simultaneous amplification, of an lysC allele coding for a feedback-resistant aspartate kinase and of the dapA, dapB, lysA and aspC genes. EP-A-0 857 784 particularly reports the increase in productivity, after simultaneous amplification, of an lysC allele coding for a feedback-resistant aspartate kinase enzym and of the lysA gene; a further improvement could be achieved by additional amplification of the ppc gene.

It is clear from the many processes described in the state of the art that there is a need for the development of novel approaches and for the improvement of existing processes for lysine production with corynebacteria.

OBJECT OF THE INVENTION

The object of the invention consists in using novel measures to provide improved L-lysine-producing strains of corynebacteria.

DETAILED DESCRIPTION OF THE INVENTION

L-Lysine is a commercially important L-amino acid which is used especially as a feed additive in animal nutrition.

When L-lysine or lysine is mentioned in the following text, it is understood as meaning not only the base but also the appropriate salts, e.g. lysine hydrochloride or lysine sulfate.

The invention provides L-lysine-producing strains of corynebacteria enhanced lysE gene (lysine export carrier gene), wherein they additionally contain genes chosen from the group comprising the dapA gene (dihydrodipicolinate synthase gene), the lysC gene (aspartate kinase gene), the dapB gene (dihydrodipicolinate reductase gene) and the pyc gene (pyruvate carboxylase gene), but especially the dapA gene and the lysC gene, which, individually or together, are enhanced and, preferably, over-expressed.

The novel DNA sequence located upstream (5' end) from the dapB gene has also been found which carries the −35 region of the dapB promoter and is advantageous for the expression of the dapB gene. It is shown as SEQ ID No. 1.

A corresponding DNA capable of replication, with the nucleotide sequence shown in SEQ ID No. 1, is therefore claimed as well.

The invention also provides the MC20 or MA16 mutations of the dapA promoter shown in SEQ ID No. 5 and SEQ ID No. 6, deposited under DSM12868 and DSM12867 respectively.

The invention also provides L-lysine-producing strains of corynebacteria with enhanced lysE gene, wherein additionally the dapA and dapB genes are simultaneously enhanced and, in particular, over-expressed.

Finally, the invention also provides L-lysine-producing strains of corynebacteria with enhanced lysE gene, wherein additionally the dapA and lysC genes are simultaneously enhanced and, in particular, over-expressed.

In this context the term "enhancement" describes the increase in the intracellular activity, in a microorganism, of one or more enzymes which are coded for by the appropriate DNA, by increasing the copy number of the gene(s), using a strong promoter or using a gene coding for an appropriate enzyme with a high activity, and optionally combining these measures.

In this context, "amplification" describes a specific procedure for achieving an enhancement whereby the number of DNA molecules carrying a gene or genes, an allele or alleles, a regulatory signal or signals or any other genetic feature(s) is increased.

A process for the preparation of L-lysine by the fermentation of these corynebacteria is also claimed.

The microorganisms which the present invention provides can prepare L-lysine from glucose, sucrose, lactose, fructose, maltose, molasses, starch or cellulose or from glycerol and ethanol, especially from glucose or sucrose. Said microorganisms are corynebacteria, especially of the genus Corynebacterium. The species *Corynebacterium glutamicum* may be mentioned in particular in the genus Corynebacterium, being known to those skilled in the art for its ability to produce amino acids. This species includes wild-type strains such as *Corynebacterium glutamicum* ATCC13032, *Brevibacterium flavum* ATCC14067, *Corynebacterium melassecola* ATCC17965 and strains or mutants derived therefrom. Examples of L-lysine-producing mutants of corynebacteria are:

*Corynebacterium glutamicum* FERM-P 1709
*Brevibacterium flavum* FERM-P 1708
*Brevibacterium lactofermentum* FERM-P 1712
*Brevibacterium flavum* FERM-P 6463
*Brevibacterium flavum* FERM-P 6464
*Corynebacterium glutamicum* DSM5714
*Corynebacterium glutamicum* DSM12866

DE-A-195 48 222 discloses the advantageous effect of over-expression of the lysE gene on L-lysine production.

The additional enhanced expression of the dapB gene or the pyc gene, or in particular an additionally enhanced expression of an lysC allele coding for a feedback-resistant aspartate kinase, or in particular an additionally enhanced expression of the dapA gene, improves L-lysine production.

The inventors have also found that, for a given over-expression of the lysE gene, the simultaneous, additionally enhanced expression of the dapA and dapB genes brings further advantages for L-lysine production.

A corresponding DNA capable of replication, with the nucleotide sequence shown in SEQ ID No. 1, is therefore claimed as well.

For a given over-expression of the lysE gene, the simultaneous, additionally enhanced expression of the dapA gene and the lysC allele is also advantageous.

An enhancement (over-expression) is achieved e.g. by increasing the copy number of the appropriate genes or mutating the promoter and regulatory region or the ribosome binding site located upstream from the structural gene. Expression cassettes incorporated upstream from the structural gene work in the same way. Inducible promoters additionally make it possible to increase the expression in the course of the formation of L-lysine by fermentation. Measures for prolonging the life of the mRNA also improve the expression. Furthermore, the enzyme activity is also enhanced by preventing the degradation of the enzyme protein, the genes or gene constructs either being located in plasmids (shuttle vectors) of variable copy number or being integrated and amplified in the chromosome. Alternatively, it is also possible to achieve an over-expression of the genes in question by changing the composition of the media and the culture technique.

Those skilled in the art will find relevant instructions inter alia in Martin et al. (Bio/Technology 5, 137–146 (1987)), Guerrero et al. (Gene 138, 35–41 (1994)), Tsuchiya and Morinaga (Bio/Technology 6, 428–430 (1988)), Eikmanns et al. (Gene 102, 93–98 (1991)), EP-0 472 869, U.S. Pat. No. 4,601,893, Schwarzer and Pühler (Bio/Technology 9, 84–87 (1991)), Reinscheid et al. (Applied and Environmental Microbiology 60, 126–132 (1994)), LaBarre et al. (Journal of Bacteriology 175, 1001–1007 (1993)), WO 96/15246, Malumbres et al. (Gene 134, 15–24 (1993)), JP-A-10-229891, Jensen and Hammer (Biotechnology and Bioengineering 58, 191–195 (1998)) or the handbook "Manual of Methods for General Bacteriology" of the American Society for Bacteriology (Washington D.C., USA, 1981) and well-known textbooks on genetics and molecular biology.

The genes from *Corynebacterium glutamicum* used according to the invention are described and can be isolated, prepared or synthesized by known methods.

Methods of localized mutagenesis are described inter alia by Higuchi et al. (Nucleic Acids Research 16: 7351–7367 (1988)) or by Silver et al. in the handbook by Innis, Glefand and Sninsky (eds.) entitled PCR Strategies (Academic Press, London, UK, 1995).

The first step in isolating a gene of interest from *C. glutamicum* is to construct a gene library of this microorganism in e.g. *E. coli* or optionally also in *C. glutamicum*. The construction of gene libraries is documented in generally well-known textbooks and handbooks. Examples which may be mentioned are the textbook by Winnacker entitled From Genes to Clones, Introduction to Gene Technology (Verlag Chemie, Weinheim, Germany, 1990) or the handbook by Sambrook et al. entitled Molecular Cloning, A Laboratory Manual (Cold Spring Harbor Laboratory Press, 1989). Bathe et al. (Molecular and General Genetics 252: 255–265 (1996)) describe a gene library of *C. glutamicum* ATCC13032 which was constructed using cosmid vector SuperCos I (Wahl et al., Proceedings of the National Academy of Sciences USA, 84: 2160–2164 (1987)) in *E. coli* K-12 NM554 (Raleigh et al., Nucleic Acids Research 16: 1563–1575 (1988)). Börmann et al. (Molecular Microbiology 6(3), 317–326) in turn describe a gene library of *C. glutamicum* ATCC13032 using cosmid pHC79 (Hohn and Collins, Gene 11, 291–298 (1980)).

A gene library of *C. glutamicum* in *E. coli* can also be constructed using plasmids like pBR322 (Bolivar, Life Sciences 25, 807–818 (1979)) or pUC19 (Norrander et al., Gene, 26: 101–106 (1983)). In the same way it is also possible to use shuttle vectors such as pJC1 (Cremer et al., Molecular and General Genetics 220, 478–480 (1990)) or pEC5 (Eikmanns et al., Gene 102, 93–98 (1991)), which replicate in *E. coli* and *C. glutamicum*. Restriction- and/or recombination-defective strains are particularly suitable hosts, an example being the *E. coli* strain DH5αmcr, which has been described by Grant et al. (Proceedings of the National Academy of Sciences, USA 87, 4645–4649 (1990)). Other examples are the restriction-defective *C. glutamicum* strains RM3 and RM4, which are described by Schäfer et al. (Applied and Environmental Microbiology 60(2), 756–759 (1994)).

The gene library is then transferred to an indicator strain by transformation (Hanahan, Journal of Molecular Biology 166, 557–580 (1983)) or electroporation (Tauch et al., FEMS Microbiological Letters, 123: 343–347 (1994)). The characteristic feature of the indicator strain is that it possesses a mutation in the gene of interest which causes a detectable phenotype, e.g. an auxotrophy. The indicator strains or mutants are obtainable from publicized sources or strain collections, e.g. the Genetic Stock Center of Yale University (New Haven, Conn., USA), or if necessary are specially prepared. An example of such an indicator strain which may be mentioned is the *E. coli* strain RDA8 requiring mesodiaminopimelic acid (Richaud et al., C. R. Acad. Sci. Paris Ser. III 293: 507–512 (1981)), which carries a mutation (dapA::Mu) in the dapA gene.

After transformation of the indicator strain with a recombinant plasmid carrying the gene of interest, and expression of the gene in question, the indicator strain becomes prototrophic in respect of the appropriate characteristic. If the cloned DNA fragment confers resistance, e.g. to an antimetabolite like S-(2-aminoethyl)cysteine, the indicator strain carrying the recombinant plasmid can be identified by selection on appropriately supplemented nutrient media.

If the nucleotide sequence of the gene region of interest is known or obtainable from a data bank, the chromosomal DNA can be isolated by known methods, e.g. as described by Eikmanns et al. (Microbiology 140, 1817–1828 (1994)), and the gene in question can be synthesized by the polymerase chain reaction (PCR) using suitable primers and cloned into a suitable plasmid vector, e.g. pCRIITOPO from Invitrogen (Groningen, The Netherlands). A summary of PCR methodology can be found in the book by Newton and Graham entitled PCR (Spektrum Akademischer Verlag, Heidelberg, Germany, 1994).

Examples of publicly accessible data banks for nucleotide sequences are that of the European Molecular Biologies Laboratories (EMBL, Heidelberg, Germany) or that of the National Center for Biotechnology Information (NCBI, Bethesda, Md., USA).

The isolation and cloning of the lysE gene from *C. glutamicum* ATCC13032, together with the nucleotide sequence, are described in DE-A-195 48 222.

The isolation, cloning and sequencing of the dapA gene from various strains of *C. glutamicum* are described by Cremer et al. (Molecular and General Genetics 220: 478–480 (1990)), by Pisabarro et al. (Journal of Bacteriology 175: 2743–2749 (1993)) and by Bonnassie et al. (Nucleic Acids Research 18, 6421 (1990)). The nucleotide sequence of the dapA gene is obtainable under accession number X53993.

The isolation, cloning and sequencing of the dapB gene from *Brevibacterium lactofermentum* are described by Pisabarro et al. (Journal of Bacteriology 175: 2743–2749 (1993)). The nucleotide sequence of the dapB gene is obtainable under accession number X67737.

The isolation, cloning and sequencing of the lysC gene and of lysC alleles coding for a feedback-resistant aspartate kinase are reported by several authors. Thus, Kalinowski et al. (Molecular and General Genetics 224: 317–324 (1990)) report the lysC allele from the *C. glutamicum* strain DM58-1. DE-A-39 43 117 reports the cloning of the lysC allele from the *C. glutamicum* strain MH20. Follettie et al. (Journal of Bacteriology 175: 4096–4103 (1993)) report the lysC allele from the *C. flavum* strain N13, which is called ask in said publication. Kalinowski et al. (Molecular Microbiology 5, 1197–1204 (1991)) report the lysC gene from *C. glutamicum* ATCC13032. The nucleotide sequences of the lysC gene and of various lysC alleles are obtainable inter alia under accession numbers X57226 and E06826.

The genes obtained in this way can then be incorporated inter alia into plasmid vectors, e.g. pJC1 (Cremer et al., Molecular and General Genetics 220, 478–480 (1990)) or pEC5 (Eikmanns et al., Gene 102, 93–98 (1991)), individually or in suitable combinations, transferred to desired strains of corynebacteria, e.g. the strain MH20-22B (Schrumpf et al., Applied Microbiology and Biotechnology 37: 566–571 (1992)), by transformation, e.g. as in Thierbach et al. (Applied Microbiology and Biotechnology 29, 356–362 (1988)), or by electroporation, e.g. as in Dunican and Shivnan (Bio/Technology 7, 1067–1070 (1989)), and expressed. The strain to be chosen can equally well be transformed with two plasmid vectors, each containing the gene or genes in question, thereby achieving the advantageous, simultaneously enhanced expression of two or more genes in addition to the known enhancement of the lysE gene.

Examples of such strains are:
the strain MH20-22B/pJC33/pEC7lysE, in which the lysE and lysC genes are expressed with simultaneous enhancement, or
the strain MH20-22B/pJC50/pEC7lysE, in which the lysE, lysC and dapA genes are expressed with simultaneous enhancement, or
the strain MH20-22B/pJC23/pEC7lysE, in which the lysE and dapA genes are expressed with simultaneous enhancement, or
the strain MH20-22B/pJC23/pEC7dapBlysE, in which the lysE, dapA and dapB genes are expressed with simultaneous enhancement.

The microorganisms prepared according to the invention can be cultivated for L-lysine production continuously or discontinuously by the batch process, the fed batch process or the repeated fed batch process. A summary of known cultivation methods is provided in the textbook by Chmiel (Bioprozesstechnik 1. Einführung in die Bioverfahrenstechnik (Bioprocess Technology 1. Introduction to Bioengineering) (Gustav Fischer Verlag, Stuttgart, 1991)) or in the textbook by Storhas (Bioreaktoren und periphere Einrichtungen (Bioreactors and Peripheral Equipment) (Vieweg Verlag, Brunswick/Wiesbaden, 1994)).

The culture medium to be used must appropriately meet the demands of the particular microorganisms. Descriptions of culture media for various microorganisms can be found in the handbook "Manual of Methods for General Bacteriology" of the American Society for Bacteriology (Washington D.C., USA, 1981).

Carbon sources which can be used are sugars and carbohydrates, e.g. glucose, sucrose, lactose, fructose, maltose, molasses, starch and cellulose, oils and fats, e.g. soya oil, sunflower oil, groundnut oil and coconut fat, fatty acids, e.g. palmitic acid, stearic acid and linoleic acid, alcohols, e.g. glycerol and ethanol, and organic acids, e.g. acetic acid. These substances can be used individually or as a mixture.

Nitrogen sources which can be used are organic nitrogen-containing compounds such as peptones, yeast extract, meat extract, malt extract, corn steep liquor, soybean flour and urea, or inorganic compounds such as ammonium sulfate, ammonium chloride, ammonium phosphate, ammonium carbonate and ammonium nitrate. The nitrogen sources can be used individually or as a mixture.

Phosphorus sources which can be used are potassium dihydrogenphosphate or dipotassium hydrogenphosphate or the corresponding sodium salts. The culture medium must also contain metal salts, e.g. magnesium sulfate or iron sulfate, which are necessary for growth. Finally, essential growth-promoting substances such as amino acids and vitamins can be used in addition to the substances mentioned above. Said feed materials can be added to the culture all at once or fed in appropriately during cultivation.

The pH of the culture is controlled by the appropriate use of basic compounds such as sodium hydroxide, potassium hydroxide or ammonia, or acid compounds such as phosphoric acid or sulfuric acid. Foaming can be controlled using antifoams such as fatty acid polyglycol esters. The stability of plasmids can be maintained by optionally adding suitable selectively acting substances, e.g. antibiotics, to the medium. Aerobic conditions are maintained by introducing oxygen or oxygen-containing gaseous mixtures, e.g. air, into the culture. The temperature of the culture is normally 20° C. to 45° C. and preferably 25° C. to 40° C. The culture is continued until L-lysine formation has reached a maximum. This objective is normally achieved within 10 hours to 160 hours.

The concentration of L-lysine formed can be determined with the aid of amino acid analyzers by means of ion exchange chromatography and postcolumn reaction with ninhydrin detection, as described by Spackmann et al. (Analytical Chemistry 30, 1190 (1958)).

The following microorganisms have been deposited in the Deutsche Sammlung für Mikroorganismen und Zellkulturen (German Collection of Microorganisms and Cell Cultures (DSMZ), Brunswick, Germany) under the terms of the Budapest Treaty:

Escherichia coli K-12 strain DH5α/pEC7lysE as DSM12871
Escherichia coli K-12 strain DH5α/pEC7dapBlysE as DSM12875
Corynebacterium glutamicum strain DSM5715/pJC23 as DSM12869
Corynebacterium glutamicum strain DSM5715aecD::dapA(MA16) as DSM12867
Corynebacterium glutamicum strain DSM5715aecD::dapA(MC20) as DSM12868

BRIEF DESCRIPTION OF THE DRAWINGS

The following Figures are attached.

Cm: chloramphenicol resistance gene
dapB: dapB gene from C. glutamicum
lysE: lysE gene from C. glutamicum
pyc: pyc gene from C. glutamicum
OriE: plasmid-coded origin of replication of E. coli
pBL: DNA fragment of plasmid pBL1
EcoRI: cleavage site of the restriction enzyme EcoRI
EcoRV: cleavage site of the restriction enzyme EcoRV
HincII: cleavage site of the restriction enzyme HincII
HindIII: cleavage site of the restriction enzyme HindIII
KpnI: cleavage site of the restriction enzyme
KpnISalI: cleavage site of the restriction enzyme
SalISmaI: cleavage site of the restriction enzyme
SmaISphI: cleavage site of the restriction enzyme SphI
PvuII: cleavage site of the restriction enzyme PvuII
BamHI: cleavage site of the restriction enzyme BamHI

EXAMPLE 1

Preparation of the DNA Coding for lysE

Chromosomal DNA was isolated from the strain ATCC13032 by the conventional methods (Eikmanns et al., Microbiology 140: 1817–1828 (1994)). The polymerase chain reaction (PCR) was used to amplify a DNA fragment carrying the lysE gene. The following primer oligonucleotides were chosen for the PCR on the basis of the lysE gene sequence known for *C. glutamicum* (Vrljic et al., Molecular Microbiology 22(5), 815–826 (1996)) (accession number X96471):

LysBam1:
5' CTC GAG AGC (GGA TCC) GCG CTG ACT CAC C 3'
LysBam2:
5' GGA GAG TAC GGC (GGA TCC) ACC GTG ACC 3'

The primers shown were synthesized by MWG Biotech (Ebersberg, Germany) and the PCR was carried out by the standard PCR method of Innis et al. (PCR Protocols. A Guide to Methods and Applications, 1990, Academic Press). The primers make it possible to amplify an approx. 1.1 kb DNA fragment carrying the lysE gene. The primers also contain the sequence for the cleavage site of the restriction endonuclease BamHI, which is indicated by brackets in the nucleotide sequence shown above.

The amplified DNA fragment of approx. 1.1 kb, carrying the lysE gene, was identified by means of electrophoresis in 0.8% agarose gel, isolated from the gel and purified with the QIAquick Gel Extraction Kit (cat. no. 28704) from Qiagen (Hilden, Germany). The fragment was then ligated by means of T4 DNA ligase from Boehringer Mannheim (Mannheim, Germany) to vector pUC18 (Norrander et al., Gene (26) 101–106 (1983)). This was done by fully cleaving vector pUC18 with the restriction endonuclease SmaI and treating it with alkaline phosphatase (Boehringer Mannheim, Mannheim, Germany). The ligation mixture was transformed to the *E. coli* strain DH5α (Hanahan, in: DNA Cloning, A Practical Approach, Vol. I, IRL-Press, Oxford, Washington D.C., USA). Plasmid-carrying cells were selected by plating the transformation mixture on LB agar (Sambrook et al., Molecular Cloning: A Laboratory Manual, 2nd ed., Cold Spring Harbor Laboratory Press, Cold Spring Harbor, N.Y.) which had been supplemented with 50 mg/l of ampicillin. Plasmid DNA was isolated from a transformant and checked by treatment with the restriction enzyme BamHI followed by agarose gel electrophoresis. The plasmid was called pUC18lysE.

EXAMPLE 2

Preparation of dapB

Chromosomal DNA was isolated from the *Corynebacterium glutamicum* strain ATCC13032 as indicated in Example 1. The sequence of the dapB gene as such from *Corynebacterium glutamicum* is known (accession number X67737). However, the published DNA sequence comprises only 56 bp upstream from the translation start, so the 5' end upstream from the translation start was additionally sequenced.

The sequencing was carried out with plasmid pJC25 (EP-B 0 435 132) using a primer oligonucleotide which binds in the region of the known dapB sequence (accession number X67737). The sequence of the sequencing primer used was:

5' GAA CGC CAA CCT TGA TTC C 3'

The sequencing was carried out by the chain termination method described by Sanger et al., Proc. Natl. Acad. Sci. USA, (74), 5463–5467 (1977). The sequencing reaction was performed with the aid of the AutoRead Sequencing Kit (Pharmacia, Freiburg). The electrophoretic analysis and detection of the sequencing products were carried out with the A.L.F. DNA sequencer from Pharmacia (Freiburg, Germany).

The DNA sequence obtained was used to choose a second primer in order to obtain further sequence data upstream from the transcription start. The following primer was chosen for this purpose:

5' CTT TGC CGC CGT TGG GTT C 3' (sic)

The sequencing reaction was carried out as described above. The novel sequence upstream from the dapB gene is shown as SEQ ID No. 1. The sequence including the nucleotide sequence of the dapB gene is shown as SEQ ID No. 2.

The polymerase chain reaction was used to amplify the dapB gene. For this purpose, two primer oligonucleotides, chosen on the basis of the known DNA sequence of the dapB gene, were synthesized by MWG Biotech:

P-dap:
5' (AAG CTT) AGG TTG TAG GCG TTG AGC 3'
dapall:
5' TTA ACT TGT TCG GCC ACA GC 3'

The 5' primer (primer P-dap) contains a HindIII cleavage site which is indicated by brackets in the sequence shown above. The PCR was carried out as in Example 1. An approx. 1.1 kb DNA fragment, which carries the dapB gene and contains a cleavage site for the restriction endonuclease HindIII at one end, was amplified in this way. The PCR fragment obtained was purified from 0.8% agarose gel (QIAquick Gel Extraction Kit from Qiagen, Hilden, Germany) and cloned into cloning vector pCR2.1TOPO (Invitrogen, Leek, The Netherlands) with the TOPO TA Cloning Kit (Invitrogen, Leek, The Netherlands, cat. no. K4550-01). The ligation mixture was transformed to the *E. coli* strain TOP10F' from Invitrogen, the transformation mixture was plated on LB agar containing kanamycin (50 mg/l), IPTG (0.16 mM) and X-Gal (64 mg/l) and kanamycin-resistant, white colonies were isolated. Plasmid DNA was isolated from a transformant with the aid of the QIAprep Spin Miniprep Kit from Qiagen and checked by cleavage with the restriction enzyme HindIII followed by agarose gel electrophoresis. The DNA sequence of the amplified DNA fragment was checked by sequencing. The sequence of the PCR product matches the sequence shown in SEQ ID No. 1. The plasmid obtained was called pCR2.1TOPOdapB.

EXAMPLE 3

Cloning of lysE into Vector pEC7

The lysE-carrying fragment from plasmid pUC18lysE (Example 1) was inserted into vector pEC7 as described below. Vector pEC7 is based on *E. coli—C. glutamicum* shuttle vector pEC5 (Eikmanns et al., Gene 102: 93–98 (1991)). The BamHI cleavage site not located in the polylinker was removed from plasmid pEC5 in the following manner: Plasmid pEC5 was partially cleaved with the restriction enzyme BamHI. The approx. 7.2 kb DNA fragment was isolated from the agarose gel and the protruding ends were filled in with Klenow polymerase (Boehringer Mannheim). The resulting DNA fragment was ligated (T4 ligase, Boehringer Mannheim). The ligation mixture was transformed to the *E. coli* strain DH5α and chloramphenicol-resistant colonies were isolated on LB agar containing chloramphenicol (50 mg/l). Plasmid DNA was isolated from a transformant (QIAprep Spin Miniprep Kit from Qiagen) and checked by restriction cleavage with the restriction enzymes BamHI and PstI. The resulting plasmid was called pEC6.

Plasmid pEC6 was fully cleaved with the restriction enzyme XhoI. A DNA fragment carrying the trp terminator was ligated to vector DNA fragment (T4 ligase, Boehringer Mannheim). The ligation mixture was transformed to the *E. coli* strain DH5α and kanamycin-resistant colonies were isolated on LB agar containing kanamycin (50 mg/l). Plasmid DNA was isolated from a transformant (QIAprep Spin Miniprep Kit from Qiagen) and checked by restriction cleavage with the restriction enzymes BamHI and XhoI. The resulting plasmid was called pEC7.

Figure 1:
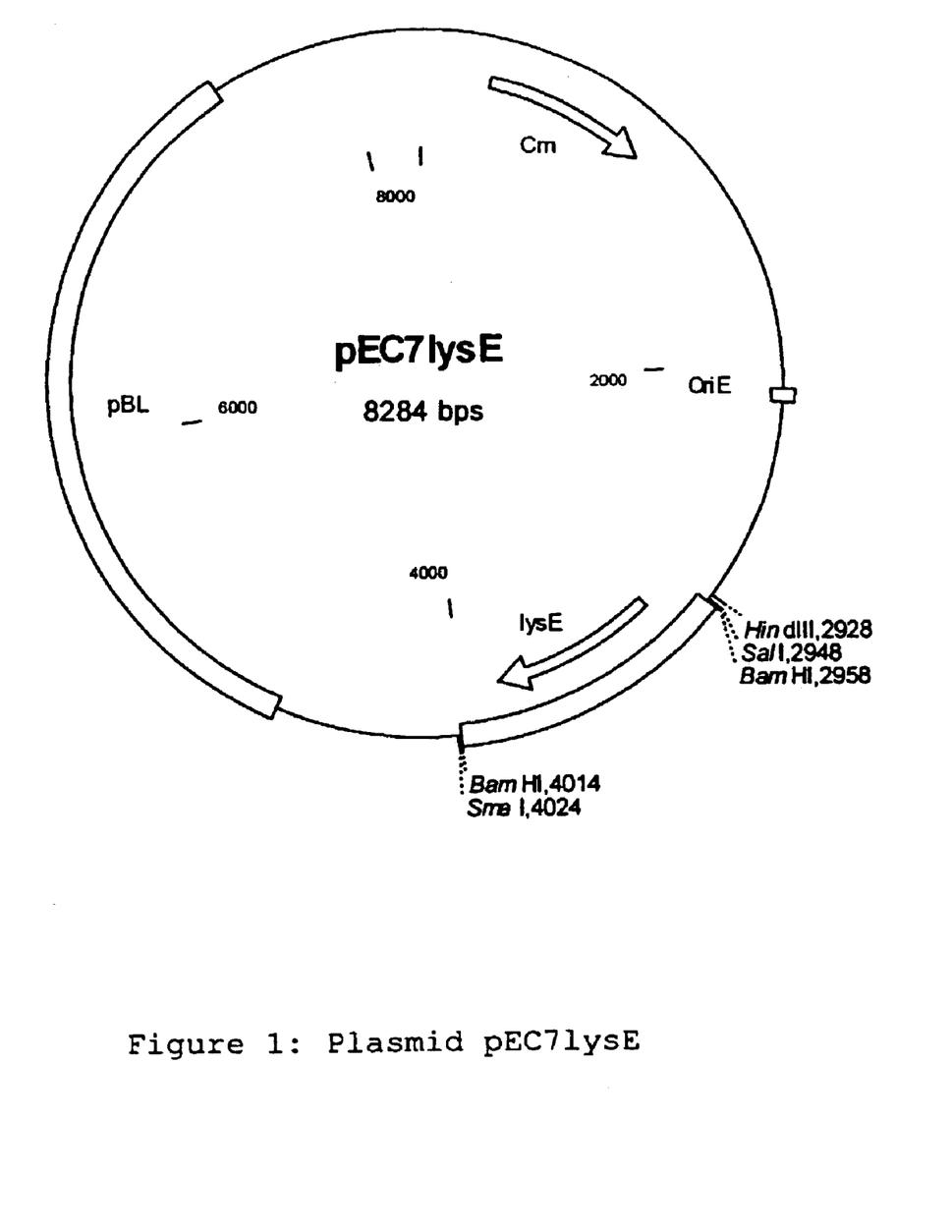
FIG. 1: Plasmid pEC7lysE

Plasmid pUC18lysE described in Example 1 was fully digested with the restriction enzyme BamHI and the 1.1 kb BamHI fragment carrying the lysE gene was isolated as in Example 1. Vector pEC7 was likewise fully cleaved with the restriction enzyme BamHI and treated with alkaline phosphatase. The BamHI vector fragment and the BamHI lysE fragment were ligated (Rapid DNA Ligation Kit, Boehringer Mannheim) and transformed to the *E. coli* strain DH5α. Plasmid-carrying transformants were selected on LB agar containing chloramphenicol (10 mg/l). Plasmid DNA was isolated (QIAprep Spin Miniprep Kit, Qiagen) and checked by restriction cleavage with the enzyme BamHI. The resulting plasmid was called pEC7lysE (FIG. 1). The strain obtained by transformation of plasmid pEC7lysE to the *E. coli* strain DH5α was called DH5α/pEC7lysE.

EXAMPLE 4

Cloning of dapB into Vector pEC7

An approx. 1.1 kb DNA fragment carrying the dapB gene was isolated from plasmid pCR2.1TOPOdapB (from Example 2). For this purpose, plasmid pCR2.1TOPOdapB was fully digested with the restriction enzyme HindIII and the approx. 1.1 kb DNA fragment carrying the dapB gene was isolated.

Figure 2:
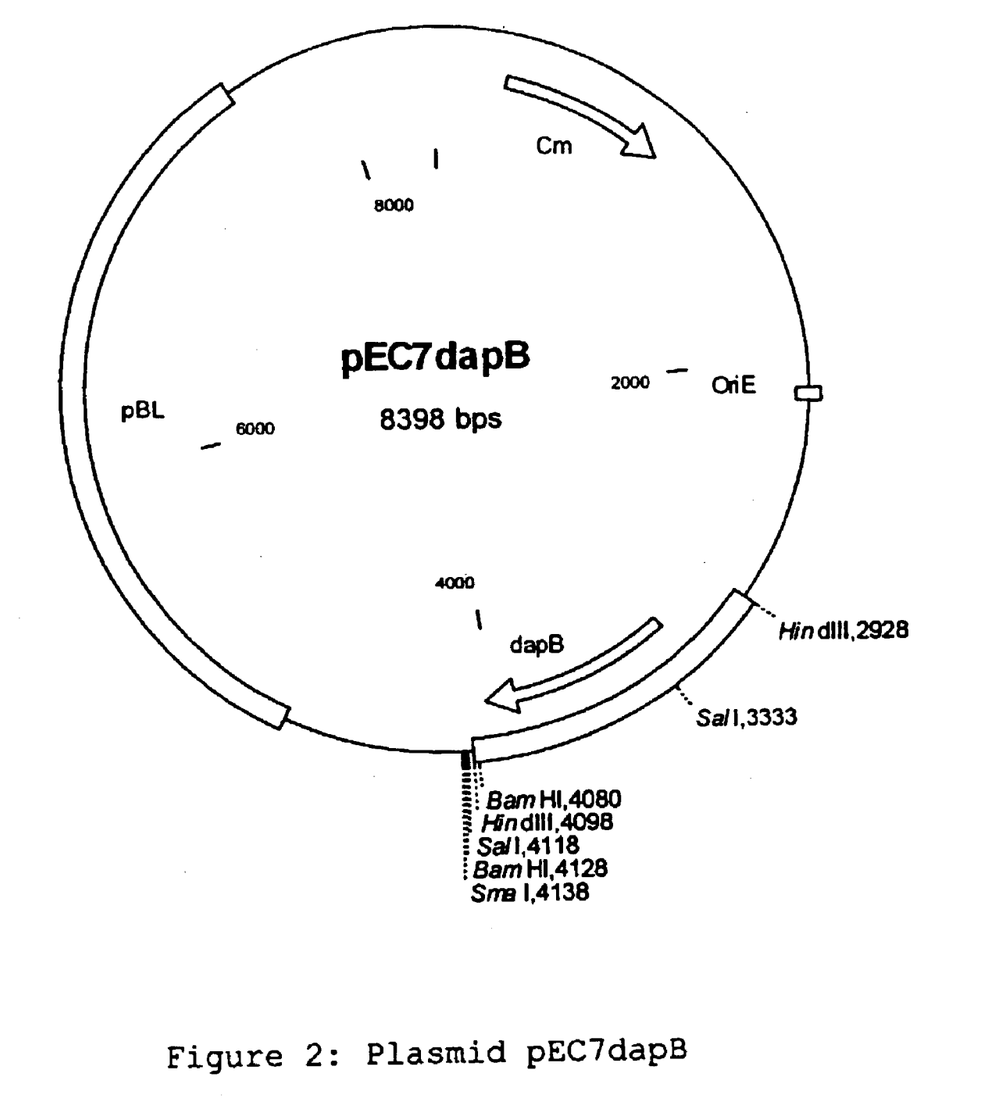
FIG. 2: Plasmid pEC7dapB

The dapB-carrying DNA fragment obtained was ligated to vector pEC7 (Example 3) (T4 DNA ligase, Boehringer Mannheim), which had also been fully digested with the restriction enzyme HindIII and treated with alkaline phosphatase (Boehringer Mannheim). The ligation mixture was transformed to the *E. coli* strain DH5α and kanamycin-resistant colonies were isolated on LB agar containing kanamycin (50 mg/l). Plasmid DNA was isolated from a transformant (QIAprep Spin Miniprep Kit from Qiagen) and checked by restriction cleavage with the restriction enzyme HindIII. The resulting plasmid was called pEC7dapB (FIG. 2). The *Escherichia coli* strain obtained was called DH5α/pEC7dapB.

EXAMPLE 5

Preparation of a Plasmid Simultaneously Containing dapB and lysE

The dapB gene was isolated as a HindIII fragment from plasmid pCR2.1TOPOdapB containing the dapB gene from *C. glutamicum* ATCC13032. To do this, the plasmid was fully digested with the restriction enzyme HindIII and the dapB-carrying DNA fragment was isolated from 0.8% agarose gel (QIAquick Gel Extraction Kit, Qiagen). Vector pEC7 (Example 3) was also fully digested with the restriction enzyme HindIII and treated with alkaline phosphatase. The 1.1 kb fragment containing dapB was ligated to the resulting linear vector fragment (T4 ligase, Boehringer Mannheim) and the ligation mixture was transformed to the *E. coli* strain DH5α. Plasmid-carrying transformants were selected on LB agar containing chloramphenicol (10 mg/l). Plasmid DNA was isolated (QIAprep Spin Miniprep Kit, Qiagen, Hilden, Germany) and checked by restriction cleavage with the restriction enzyme HindIII.

The resulting plasmid was called pEC7lysEdapB. This plasmid is capable of autonomous replication in *Escherichia coli* and in Corynebacterium and confers resistance to the antibiotic chloramphenicol on its host.

Figure 3:
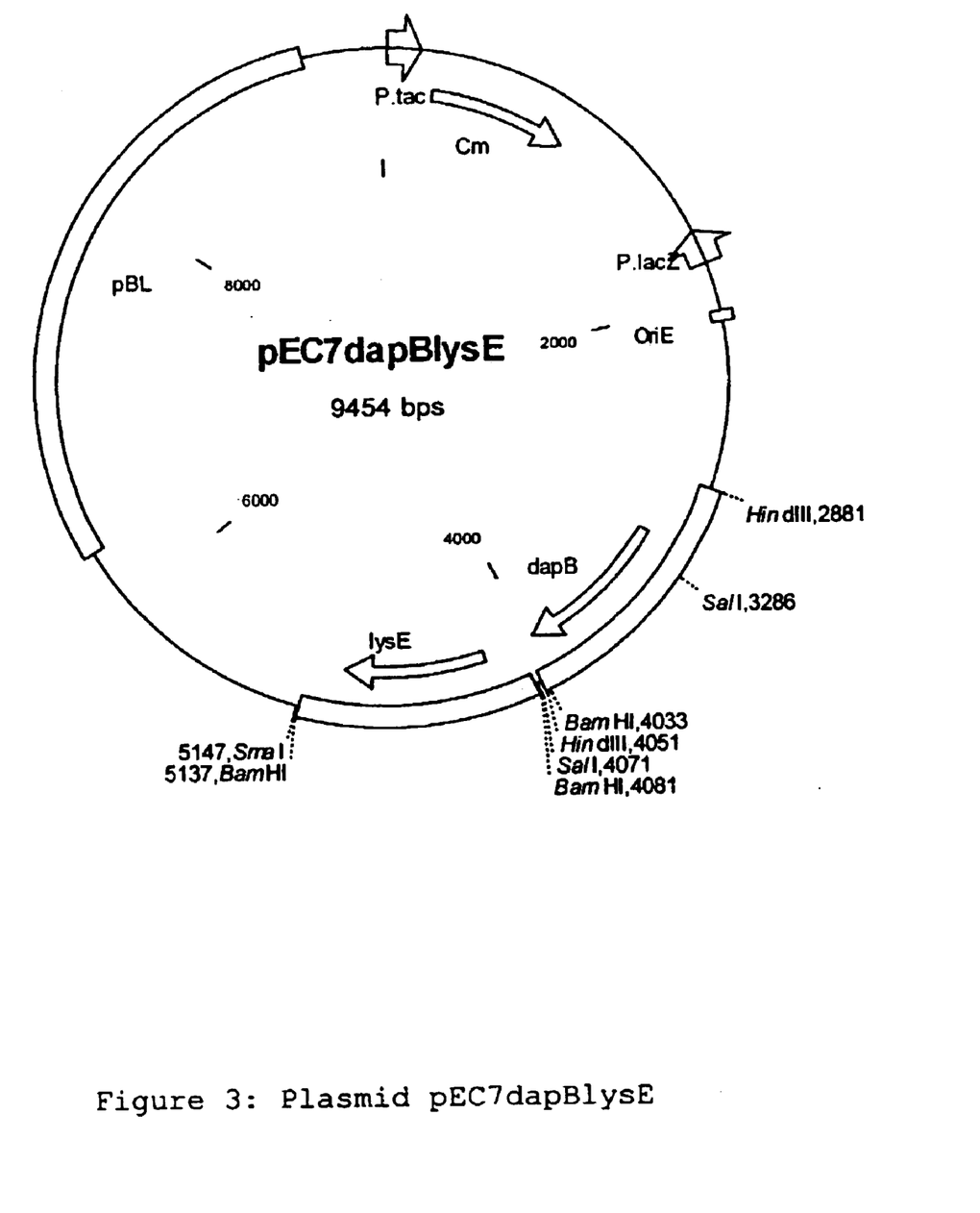
FIG. 3: Plasmid pEC7dapBlysE The abbreviations used in the Figures are defined as follows.

As shown in FIG. 3, plasmid pEC7lysEdapB simultaneously contains the dapB gene, which codes for dihydrodipicolinate reductase, and the lysE gene, which codes for the lysine exporter. The strain obtained by transformation of the *E. coli* strain DH5α with pEC7lysEdapB was called DH5α/pEC7lysEdapB.

EXAMPLE 6
Transformation of the Strain MH20-22B with Plasmids pJC1, pJC33 and pJC50

Plasmid pJC1 is a plasmid capable of replication in *Escherichia coli* and *Corynebacterium glutamicum* (Cremer et al., Molecular and General Genetics 220: 478–480 (1990)). Plasmid pJC33 (Cremer et al., Applied and Environmental Microbiology 57(6), 1746–1752 (1991)), which carries the lysC(Fbr) gene from the *C. glutamicum* strain MH20-22B, is derived therefrom.

Plasmid pJC50 is also based on vector pJC1 and carries the lysC(FBR) gene from *C. glutamicum* MH20-22B and the dapA gene from *C. glutamicum* ATCC13032 (DE-A-39 43 117).

Plasmids pJC1, pJC33 and pJC50 were introduced into the strain MH20-22B by the electroporation method (Haynes and Britz, FEMS Microbiology Letters (61) 329–334 (1989)). The *C. glutamicum* strain MH20-22B is an AEC-resistant lysine producer deposited under the number DSM5715.

The transformants obtained by means of electroporation were isolated on selection agar (LBHIS agar (18.5 g/l of brain-heart infusion broth, 0.5 M sorbitol, 5 g/l of bacto tryptone, 2.5 g/l of bacto yeast extract, 5 g/l of NaCl, 18 g/l of bacto agar)) containing 15 mg/l of kanamycin. Plasmid DNA was isolated by the conventional methods (Peters-Wendisch et al., Microbiology 144, 915–927 (1998)), cleaved with suitable restriction endonucleases and checked. The strains obtained were called MH20-22B/pJC1, MH20-22B/pJC33 and MH20-22B/pJC50.

EXAMPLE 7
Transformation with Plasmids pEC7lysE and pEC7dapBlysE

The strains prepared in Example 6 were subsequently provided with a second plasmid.

Plasmids pEC7lysE and pEC7dapBlysE were introduced by the electroporation method into the strains MH20-22B/pJC1, MH20-22B/pJC33 and MH20-22B/pJC50 described.

The transformed bacteria are selected on the basis of the antibiotic resistance of the plasmids they contain. The transformants obtained by means of electroporation were isolated on selection agar (LBHIS agar containing 15 mg/l of kanamycin and 7.5 mg/l of chloramphenicol). Plasmid DNA was isolated, cleaved with suitable restriction endonucleases and checked.

EXAMPLE 8
Preparation of Lysine

The various *C. glutamicum* strains obtained in Example 7 were cultivated in a nutrient medium suitable for lysine production and the lysine content of the culture supernatant was determined.

This was done by first incubating the various strains on agar plates with the appropriate antibiotics (brain-heart agar containing kanamycin (25 mg/l), chloramphenicol (10 mg/l)) for 24 hours at 33° C. These agar plate cultures were used to inoculate a preculture (10 ml of medium in a 100 ml conical flask). Complete medium CgIII was used as the preculture medium. Kanamycin (25 mg/l) and chloramphenicol (10 mg/l) were added. The preculture was incubated for 24 hours at 33° C. on a shaker at 240 rpm. This preculture was used to inoculate a main culture to give an initial OD (660 nm) of 0.2 OD. Medium MM was used for the main culture.

| Medium MM | |
|---|---|
| CSL (corn steep liquor) | 5 g/l |
| MOPS (morpholinopropane sulfonic acid) | 20 g/l |
| Glucose | 50 g/l (autoclave separately) |
| Salts: | |
| $(NH_4)_2SO_4$ | 25 g/l |
| $KH_2PO_4$ | 0.1 g/l |
| $MgSO_4 \star 7H_2O$ | 1.0 g/l |
| $CaCl_2 \star 2H_2O$ | 10 mg/l |
| $FeSO_4 \star 7H_2O$ | 10 mg/l |
| $MnSO_4 \star H_2O$ | 5.0 mg/l |
| Biotin | 0.3 mg/l (sterile-filtered) |
| Thiamine★HCl | 0.2 mg/l (sterile-filtered) |
| $CaCO_3$ | 25 g/l |

CSL, MOPS and the salt solution are adjusted to pH 7 with aqueous ammonia and autoclaved. The sterile substrate and vitamin solutions and the dry-autoclaved $CaCO_3$ are then added.

Cultivation is carried out in a volume of 10 ml in a 100 ml conical flask with baffles. Kanamycin (25 mg/l) and chloramphenicol (10 mg/l) were added. Cultivation proceeded at 33° C. and 80% atmospheric humidity.

After 48 hours the OD was measured at a wavelength of 660 nm with a Biomek 1000 (Beckmann Instruments GmbH, Munich). The amount of lysine formed was determined with an amino acid analyzer from Eppendorf-BioTronik (Hamburg, Germany) by means of ion exchange chromatography and postcolumn derivatization with ninhydrin detection. The glucose content was determined with a sugar analyzer from Skalar Analytik GmbH (Erkelenz, Germany).

The experimental results are shown in Table 1.

TABLE 1

| Strain | Gene | OD (660 nm) | Lysine-HCl g/l |
|---|---|---|---|
| DSM5715/pJCl/pEC7lysE | lysE | 9.1 | 11.1 |
| DSM5715/pJC33/pEC7lysE | lysE, lysC | 8.7 | 12.2 |
| DSM5715/pJC50/pEC7lysE | lysE, lysC, dapA | 9.1 | 12.7 |
| DSM5715/pJC23/pEC7lysE | lysE, dapA | 10.2 | 13.3 |
| DSM5715/pJC23/pEC7dapBlysE | lysE, dapA, dapB | 10.9 | 15.4 |

EXAMPLE 9
Cloning of the aecD Gene into Vector pUC18

Plasmid pSIR21 (Rossol, Thesis, University of Bielefeld 1992) was fully cleaved with the enzymes BglII and EcoRV and the 1.4 kb DNA fragment containing the aecD gene (accession number M89931) (Rossol and Pühler, Journal of Bacteriology 174 (9), 2968–2977 (1992)) from *C. glutamicum* ATCC13032 was isolated. The isolated DNA fragment was ligated to plasmid pUC18 (which had been fully digested with the enzymes BamHI and SmaI) using T4 DNA ligase, as described in Sambrook et al. (Molecular Cloning: A Laboratory Manual (1989), Cold Spring Harbor Laboratory Press). The ligation mixture was transformed to the *E. coli* strain DH5α. The transformants were selected on brain-heart agar plates containing 100 mg/l of ampicillin. Plasmid DNA was isolated from one colony. The plasmid obtained was called pUC18::aecD.

EXAMPLE 10
Cloning of the dapA Gene into Plasmid pSP72

A dapA gene fragment is isolated from plasmid pJC20 (Cremer, J., Thesis 1989, University of Düsseldorf) as an SphI-BamHI fragment. Vector pSP72 (Promega Corporation, USA) was fully cleaved with the enzymes SphI and BamHI and treated with alkaline phosphatase. The dapA-carrying fragment was ligated to this vector using T4 DNA ligase. The DNA was then transformed to the *E. coli* strain XL1 Blue (Bullock, Fernandez and Short, BioTechniques (5), 376–379 (1987)). The transformants were selected on LB medium containing 100 mg/l of ampicillin. Plasmid DNA was isolated from one transformant and called pSP72::dapA.

EXAMPLE 11
Mutagenesis of the dapA Promoter and Preparation of Plasmids pSP72::dapA(MC20) and pSP72::dapA(MA16)

The Quickchange site directed mutagenesis kit from Stratagene was used for the mutagenesis of the promoter region. The following primers were constructed with the aid of said dapA sequence and used for the mutagenesis:
For the Preparation of pSP72::dapA(MC20)
  Primer dap1 for MC20
CCA AAT GAG AGA TGG TAA CCT TGA ACT CTA TGA GCA
  Primer dap2 for MC20
GTG CTC ATA GAG TTC AAG GTT ACC ATC TTC CCT CAT TTG G
For the Preparation of pSP72::dapA(MA16)
  Primer dap3 for MA16
CCA AAT GAG GGA AGA AGG TAT AAT TGA ACT CTA TGA GCA
  Primer dap4 for MA16
GTG CTC ATA GAG TTC AAT TAT ACC TTC TTC CCT CAT TTG G The PCR was carried out as indicated by the manufacturer of the Quickchange site directed mutagenesis kit (Stratagene) using plasmid pSP72::dapA (from Example 10) as the template.

The mutagenesis mixtures were transformed to the *E. coli* strain XL1 Blue. The transformants were selected on LB medium containing 100 mg/l of carbenicillin. Plasmid DNA was isolated from one transformant and the loss of the BstEII cleavage site was controlled by BstEII digestion. Plasmids no longer carrying a BstEII cleavage site exhibited the desired mutation.

The plasmids obtained were transformed to the dapA-defective *E. coli* mutant RDA8. The transformation mixtures were plated on LB containing 100 mg/l of carbenicillin in order to test the complementation of the dapA mutation. DNA was isolated from one transformant in each case and the plasmids obtained were called pSP72::dapA(MC20) and pSP72::dapA(MA16). The plasmids were sequenced by the chain termination method described in Sanger et al., Proceedings of the National Academy of Sciences of the USA (74), 5463–5467 (1977), using the reverse and universal sequencing primers. The sequencing reaction was performed with the aid of the AutoRead Sequencing Kit (Pharmacia, Freiburg). The electrophoretic analysis and detection of the sequencing products were carried out with the A.L.F. DNA sequencer (Pharmacia, Freiburg).

EXAMPLE 12
Preparation of Plasmids pK19mobsacBaecD::dapA(MC20) and pK19mobsacBaecD::dapA(MA16) (Recloning of the Mutagenized Fragments)

Plasmids pSP72::dapA(MC20) and pSP72::dapA(MA16) (from Example 11) were fully cleaved with the restriction enzymes PvuII and SmaI. The 1450 bp PvuII-SmaI fragments carrying the dapA gene with the mutated MC20 or MA16 promoter were ligated to StuI-cleaved vector pUC18::aecD (from Example 9) using T4 DNA ligase. The ligation mixture was transformed to the *E. coli* strain DH5α. The transformants were selected on LB medium containing 100 mg/l of ampicillin. Plasmid DNA was isolated from one transformant in each case to give plasmids pUC18aecD::dapA(MC20) and pUC18aecD::dapA(MA16).

Plasmids pUC18aecD::dapA(MC20) and pUC18aecD::dapA(MA16) were partially cleaved with the restriction enzyme EcoRI and fully cleaved with the enzyme SalI to give the 3.0 kb fragment carrying aecD::dapA (MA16) or aecD::dapA(MC20). The fragment was ligated to vector pK19mobsacB (which had been cleaved and treated with alkaline phosphatase) (Schäfer et al., Gene (145), 69–73 (1994)) using T4 DNA ligase. The ligation mixture was transformed to the *E. coli* strain DH5 (Hanahan (1985), in: DNA Cloning. A Practical Approach, vol. I, IRL-Press, Oxford, Washington D.C., USA). The transformants were selected on LB medium containing 50 mg/l of kanamycin. Plasmid DNA was isolated from one transformant in each case to give plasmids pK19mobsacBaecD::dapA(MC20) and pK19mobsacBaecD::dapA(MA16).

The plasmid DNA was transformed to the *E. coli* strain S17-1 (Simon, Priefer and Pühler, Bio/Technology (1), 784–791 (1983)). The transformants were selected on LB medium containing 50 mg/l of kanamycin. Plasmid DNA was isolated from one transformant in each case and checked. The strains obtained were called S17-1/pK19mobsacBaecD::dapA(MC20) and S17-1/pK19mobsacBaecD::dapA(MA16).

EXAMPLE 13
Preparation of the *C. glutamicum* Strains DSM5715aecD::dapA(MC20) and DSM5715aecD::dapA(MA16)

Plasmids pK19mobsacBaecD::dapA(MC20) and pK19mobsacBaecD::dapA(MA16) were transferred from S17-1/pK19mobsacBaecD::dapA(MC20) and 817-1/pK19mobsacBaecD::dapA(MA16) (from Example 12) to the *C. glutamicum* strain DSM5715 by the conjugation method (Schäfer et al., Journal of Bacteriology (172), 1663–1666 (1990)). For selection of the transconjugants, the conjugation mixtures were plated on brain-heart medium containing nalidixic acid and kanamycin. The transconjugants obtained were incubated overnight in 10 ml of brain-heart medium. Aliquots were then plated on plates containing sucrose (brain-heart agar containing 10% of sucrose) in order to select for loss of sucrose sensitivity. Sucrose-resistant clones were isolated and checked again on agar plates containing chloramphenicol and kanamycin (brain-heart medium containing 15 mg/l of kanamycin and brain-heart medium containing 10 mg/l of chloramphenicol).

Colonies exhibiting the following phenotype were isolated:

sucrose resistant kanamycin sensitive chloramphenicol sensitive

The insertion of the dapA gene fragment into the aecD gene was checked by the Southern blot method (Sambrook et al., Molecular Cloning: A Laboratory Manual (1989), Cold Spring Harbor Laboratory Press).

EXAMPLE 14

Preparation of the *C. glutamicum* Strains DSM5715aecD::dapA(MC20)/pEC7lysE, DSM5715aecD::dapA(MA16)/pEC7lysE, DSM5715aecD::dapA(MC20)/pEC7, DSM5715aecD::dapA(MA16)/pEC7 and DSM5715/pEC7

As described in Example 3, the lysE gene is present in vector pEC7. This plasmid pEC7lysE and plasmid pEC7 were introduced into the strains DSM5715aecD::dapA(MC20), DSM5715aecD::dapA(MA16) and DSM5715 (from Example 13) by means of electroporation (Haynes 1989, FEMS Microbiology Letters 61, 329–334) to give *C. glutamicum* DSM5715aecD::dapA(MC20)/pEC7lysE, DSM5715aecD::dapA(MA16)/pEC7lysE, DSM5715aecD::dapA(MC20)/pEC7, DSM5715aecD::dapA(MA16)/pEC7 and DSM5715/pEC7. The transformants were selected on brain-heart agar containing 25 mg/l of kanamycin. Plasmid DNA was isolated from one transformant in each case and checked.

The following strains were obtained in this way:

DSM5715aecD::dapA(MC20)/pEC7lysE,
DSM5715aecD::dapA(MA16)/pEC7lysE,
DSM5715aecD::dapA(MC20)/pEC7,
DSM5715aecD::dapA(MA16)/pEC7, and
DSM5715/pEC7.

EXAMPLE 15

Preparation of Lysine with the Strains Prepared in Example 14

After precultivation in CgIII medium (Kase & Nakayama, Agricultural and Biological Chemistry 36 (9), 1611–1621 (1972)), the strains DSM5715aecD::dapA(MC20)/pEC7lysE, DSM5715aecD::dapA(MA16)/pEC7lysE, DSM5715aecD::dapA(MC20)/pEC7, DSM5715aecD::dapA(MA16)/pEC7 and DSM5715/pEC7 were cultivated in MM production medium as described in Example 8. After incubation for 48 hours, the optical density at 660 nm and the concentration of L-lysine formed were determined.

The experimental results are shown in Table 2.

TABLE 2

| Strain | OD (660 nm) | Lysine.HCl g/l |
|---|---|---|
| DSM5715aecD::dapA(MC20)/pEC7lysE | 13.3 | 13.8 |
| DSM5715aecD::dapA(MA16)/pEC7lysE | 12.4 | 14.3 |
| DSM5715/pEC7 | 13.3 | 11.5 |
| DSM5715aecD::dapA(MA16)/pEC7 | 13.3 | 12.9 |
| DSM5715aecD::dapA(MC20)/pEC7 | 14.0 | 12.8 |

What is claimed is:

1. A process for the preparation of L-lysine by fermentation comprising the following steps:

a) fermentation of L-lysine producing corynebacteria with an enhanced lysE gene, in which additionally genes selected from the group consisting of dapA gene, the lysC gene, the pyc gene and the dapB gene, individually or together, are enhanced, b) enrichment of L-lysine in the medium of in the cells of the bacteria, and c) isolation of L-lysine.

* * * * *

SEQUENCE LISTING

<160> NUMBER OF SEQ ID NOS: 16

<210> SEQ ID NO 1
<211> LENGTH: 795
<212> TYPE: DNA
<213> ORGANISM: Corynebacterium glutamicum
<220> FEATURE:
<221> NAME/KEY: misc_feature
<222> LOCATION: (1)..(795)
<223> OTHER INFORMATION: DNA upstream of dapB
<220> FEATURE:
<221> NAME/KEY: -35_signal
<222> LOCATION: (774)..(779)

<400> SEQUENCE: 1

```
ctgcagcaat gagaccgagt aatttcgggg ttgaccagat acaccaatga gaacttggga      60
acgggcttca aaaatactgg tgaagttgat gtcttcaaca atgcctgcac caggatatga    120
tccggtatcg atacctggaa cgacaacctg atcaggatat ccagtgcctt gaatattgac    180
gttgaggaag gaatcaccag ccatctcaac tggaagacct gacgcctgct gaattggatc    240
agtggcccaa tcgacccacc aaccaggttg gccattaccg gcgatatcaa aaacaactcg    300
tgtgaacgtt tcgtgctcgg caacgcggat gccagcgatc gacatatcgg agtcaccaac    360
ttgagcctgc tgcttctgat ccatcgacgg ggaacccaac ggcggcaaag cagtggggga    420
aggggggagt ttggtgcact ctgaaccgag tggtctctga agtggtaggc gacggggcag    480
ctatctgaag gcgtgcgagt tgtggtgacc gggttagcgg tttcagtttc tgtcacaact    540
ggagcaggac tagcagaggt tgtaggcgtt gagccgcttc catcacaagc acttaaaagt    600
```

-continued

```
aaagaggcgg aaaccacaag cgccaaggaa ctactgcgga acgggcggtg aagggcaact    660
taagtctcat atttcaaaca tagttccacc tgtgtgatta atccctagaa cggaacaaac    720
tgatgaacaa tcgttaacaa cacagaccaa aacggtcagt taggtatgga tatcagcacc    780
ttctgaacgg gtacg                                                     795
```

<210> SEQ ID NO 2
<211> LENGTH: 1815
<212> TYPE: DNA
<213> ORGANISM: Corynebacterium glutamicum
<220> FEATURE:
<221> NAME/KEY: -35_signal
<222> LOCATION: (774)..(779)
<220> FEATURE:
<221> NAME/KEY: -10_signal
<222> LOCATION: (798)..(803)
<220> FEATURE:
<221> NAME/KEY: CDS
<222> LOCATION: (851)..(1594)

<400> SEQUENCE: 2

```
ctgcagcaat gagaccgagt aatttcgggg ttgaccagat acaccaatga gaacttggga    60
acgggcttca aaaatactgg tgaagttgat gtcttcaaca atgcctgcac caggatatga   120
tccggtatcg atacctggaa cgacaacctg atcaggatat ccagtgcctt gaatattgac   180
gttgaggaag gaatcaccag ccatctcaac tggaagacct gacgcctgct gaattggatc   240
agtggcccaa tcgacccacc aaccaggttg gccattaccg gcgatatcaa aaacaactcg   300
tgtgaacgtt tcgtgctcgg caacgcggat gccagcgatc gacatatcgg agtcaccaac   360
ttgagcctgc tgcttctgat ccatcgacgg gaacccaac ggcggcaaag cagtgggggga    420 agggggggagt ttggtgcact ctgaaccgag tggtctctga agtggtaggc gacggggcag   480
ctatctgaag gcgtgcgagt tgtggtgacc gggttagcgg tttcagtttc tgtcacaact   540
ggagcaggac tagcagaggt tgtaggcgtt gagccgcttc catcacaagc acttaaaagt   600
aaagaggcgg aaaccacaag cgccaaggaa ctactgcgga acgggcggtg aagggcaact   660
taagtctcat atttcaaaca tagttccacc tgtgtgatta atccctagaa cggaacaaac   720
tgatgaacaa tcgttaacaa cacagaccaa aacggtcagt taggtatgga tatcagcacc   780
ttctgaacgg gtacgtctag actggtgggc gtttgaaaaa ctcttcgccc cacgaaaatg   840
aaggagcata atg gga atc aag gtt ggc gtt ctc gga gcc aaa ggc cgt       889
              Met Gly Ile Lys Val Gly Val Leu Gly Ala Lys Gly Arg
                1               5                  10 gtt ggt caa act att gtg gca gca gtc aat gag tcc gac gat ctg gag     937
Val Gly Gln Thr Ile Val Ala Ala Val Asn Glu Ser Asp Asp Leu Glu
 15                  20                  25 ctt gtt gca gag atc ggc gtc gac gat gat ttg agc ctt ctg gta gac     985
Leu Val Ala Glu Ile Gly Val Asp Asp Asp Leu Ser Leu Leu Val Asp
 30                  35                  40                  45 aac ggc gct gaa gtt gtc gtt gac ttc acc act cct aac gct gtg atg    1033
Asn Gly Ala Glu Val Val Val Asp Phe Thr Thr Pro Asn Ala Val Met
                 50                  55                  60 ggc aac ctg gag ttc tgc atc aac aac ggc att tct gcg gtt gtt gga    1081
Gly Asn Leu Glu Phe Cys Ile Asn Asn Gly Ile Ser Ala Val Val Gly
         65                  70                  75 acc acg ggc ttc gat gat gct cgt ttg gag cag gtt cgc gac tgg ctt    1129
Thr Thr Gly Phe Asp Asp Ala Arg Leu Glu Gln Val Arg Asp Trp Leu
     80                  85                  90 gaa gga aaa gac aat gtc ggt gtt ctg atc gca cct aac ttt gct atc    1177
Glu Gly Lys Asp Asn Val Gly Val Leu Ile Ala Pro Asn Phe Ala Ile
```

-continued

```
            95                  100                 105
tct gcg gtg ttg acc atg gtc ttt tcc aag cag gct gcc cgc ttc ttc      1225
Ser Ala Val Leu Thr Met Val Phe Ser Lys Gln Ala Ala Arg Phe Phe
110                 115                 120                 125 gaa tca gct gaa gtt att gag ctg cac cac ccc aac aag ctg gat gca      1273
Glu Ser Ala Glu Val Ile Glu Leu His His Pro Asn Lys Leu Asp Ala
                130                 135                 140 cct tca ggc acc gcg atc cac act gct cag ggc att gct gcg gca cgc      1321
Pro Ser Gly Thr Ala Ile His Thr Ala Gln Gly Ile Ala Ala Ala Arg
            145                 150                 155 aaa gaa gca ggc atg gac gca cag cca gat gcg acc gag cag gca ctt      1369
Lys Glu Ala Gly Met Asp Ala Gln Pro Asp Ala Thr Glu Gln Ala Leu
        160                 165                 170 gag ggt tcc cgt ggc gca agc gta gat gga atc ccg gtt cat gca gtc      1417
Glu Gly Ser Arg Gly Ala Ser Val Asp Gly Ile Pro Val His Ala Val
    175                 180                 185 cgc atg tcc ggc atg gtt gct cac gag caa gtt atc ttt ggc acc cag      1465
Arg Met Ser Gly Met Val Ala His Glu Gln Val Ile Phe Gly Thr Gln
190                 195                 200                 205 ggt cag acc ttg acc atc aag cag gac tcc tat gat cgc aac tca ttt      1513
Gly Gln Thr Leu Thr Ile Lys Gln Asp Ser Tyr Asp Arg Asn Ser Phe
                210                 215                 220 gca cca ggt gtc ttg gtg ggt gtg cgc aac att gca cag cac cca ggc      1561
Ala Pro Gly Val Leu Val Gly Val Arg Asn Ile Ala Gln His Pro Gly
            225                 230                 235 cta gtc gta gga ctt gag cat tac cta ggc ctg taaaggctca tttcagcagc    1614
Leu Val Val Gly Leu Glu His Tyr Leu Gly Leu
        240                 245 gggtggaatt ttttaaaagg agcgtttaaa ggctgtggcc gaacaagtta aattgagcgt    1674
ggagttgata gcgtgcagtt cttttactcc acccgctgat gttgagtggt caactgatgt    1734
tgagggcgcg gaagcactcg tcgagtttgc gggtcgtgcc tgctacgaaa cttttgataa    1794
gccgaaccct cgaactgctt c                                              1815
```

<210> SEQ ID NO 3
<211> LENGTH: 248
<212> TYPE: PRT
<213> ORGANISM: Corynebacterium glutamicum

<400> SEQUENCE: 3

```
Met Gly Ile Lys Val Gly Val Leu Gly Ala Lys Gly Arg Val Gly Gln
1               5                   10                  15

Thr Ile Val Ala Ala Val Asn Glu Ser Asp Asp Leu Glu Leu Val Ala
            20                  25                  30

Glu Ile Gly Val Asp Asp Leu Ser Leu Leu Val Asp Asn Gly Ala
        35                  40                  45

Glu Val Val Val Asp Phe Thr Thr Pro Asn Ala Val Met Gly Asn Leu
    50                  55                  60

Glu Phe Cys Ile Asn Asn Gly Ile Ser Ala Val Val Gly Thr Thr Gly
65                  70                  75                  80

Phe Asp Asp Ala Arg Leu Glu Gln Val Arg Asp Trp Leu Glu Gly Lys
                85                  90                  95

Asp Asn Val Gly Val Leu Ile Ala Pro Asn Phe Ala Ile Ser Ala Val
            100                 105                 110

Leu Thr Met Val Phe Ser Lys Gln Ala Ala Arg Phe Phe Glu Ser Ala
        115                 120                 125

Glu Val Ile Glu Leu His His Pro Asn Lys Leu Asp Ala Pro Ser Gly
```

```
                    130                 135                 140
Thr Ala Ile His Thr Ala Gln Gly Ile Ala Ala Ala Arg Lys Glu Ala
145                 150                 155                 160

Gly Met Asp Ala Gln Pro Asp Ala Thr Glu Gln Ala Leu Glu Gly Ser
                165                 170                 175

Arg Gly Ala Ser Val Asp Gly Ile Pro Val His Ala Val Arg Met Ser
            180                 185                 190

Gly Met Val Ala His Glu Gln Val Ile Phe Gly Thr Gln Gly Gln Thr
        195                 200                 205

Leu Thr Ile Lys Gln Asp Ser Tyr Asp Arg Asn Ser Phe Ala Pro Gly
    210                 215                 220

Val Leu Val Gly Val Arg Asn Ile Ala Gln His Pro Gly Leu Val Val
225                 230                 235                 240

Gly Leu Glu His Tyr Leu Gly Leu
                245

<210> SEQ ID NO 4
<211> LENGTH: 79
<212> TYPE: DNA
<213> ORGANISM: Corynebacterium glutamicum
<220> FEATURE:
<221> NAME/KEY: misc_feature
<222> LOCATION: (1)..(79)
<223> OTHER INFORMATION: dapA wild type promoter

<400> SEQUENCE: 4
gttaggtttt ttgcggggtt gtttaacccc caaatgaggg aagaaggtaa ccttgaactc    60
tatgagcaca ggtttaaca                                                79

<210> SEQ ID NO 5
<211> LENGTH: 79
<212> TYPE: DNA
<213> ORGANISM: Artificial
<220> FEATURE:
<221> NAME/KEY: misc_feature
<222> LOCATION: (1)..(79)
<223> OTHER INFORMATION: dapA promoter of C. glutamicum carrying the MC20
      mutation
<220> FEATURE:
<221> NAME/KEY: mutation
<222> LOCATION: (45)

<400> SEQUENCE: 5
gttaggtttt ttgcggggtt gtttaacccc caaatgaggg aagatggtaa ccttgaactc    60
tatgagcaca ggtttaaca                                                79

<210> SEQ ID NO 6
<211> LENGTH: 80
<212> TYPE: DNA
<213> ORGANISM: Artificial
<220> FEATURE:
<221> NAME/KEY: misc_feature
<222> LOCATION: (1)..(80)
<223> OTHER INFORMATION: dapA promoter of C. glutamicum carrying the
      MA16 mutation
<220> FEATURE:
<221> NAME/KEY: mutation
<222> LOCATION: (35)..(53)

<400> SEQUENCE: 6
gttaggtttt ttgcggggtt gtttaacccc caaaatgagg gaagaaggta taattgaact    60
ctatgagcac aggtttaaca                                               80
```

```
<210> SEQ ID NO 7
<211> LENGTH: 28
<212> TYPE: DNA
<213> ORGANISM: Artificial
<220> FEATURE:
<221> NAME/KEY: misc_feature
<222> LOCATION: (1)..(28)
<223> OTHER INFORMATION: PCR primer

<400> SEQUENCE: 7
ctcgagagcg gatccgcgct gactcacc                                              28

<210> SEQ ID NO 8
<211> LENGTH: 27
<212> TYPE: DNA
<213> ORGANISM: Artificial
<220> FEATURE:
<221> NAME/KEY: misc_feature
<222> LOCATION: (1)..(27)
<223> OTHER INFORMATION: PCR primer

<400> SEQUENCE: 8
ggagagtacg gcggatccac cgtgacc                                               27

<210> SEQ ID NO 9
<211> LENGTH: 19
<212> TYPE: DNA
<213> ORGANISM: Artificial
<220> FEATURE:
<221> NAME/KEY: misc_feature
<222> LOCATION: (1)..(19)
<223> OTHER INFORMATION: sequencing primer

<400> SEQUENCE: 9
gaacgccaac cttgattcc                                                        19

<210> SEQ ID NO 10
<211> LENGTH: 19
<212> TYPE: DNA
<213> ORGANISM: Artificial
<220> FEATURE:
<221> NAME/KEY: misc_feature
<222> LOCATION: (1)..(19)
<223> OTHER INFORMATION: sequencing primer

<400> SEQUENCE: 10
ctttgccgcc gttgggttc                                                        19

<210> SEQ ID NO 11
<211> LENGTH: 24
<212> TYPE: DNA
<213> ORGANISM: Artificial
<220> FEATURE:
<221> NAME/KEY: misc_feature
<222> LOCATION: (1)..(24)
<223> OTHER INFORMATION: PCR primer

<400> SEQUENCE: 11
aagcttaggt tgtaggcgtt gagc                                                  24

<210> SEQ ID NO 12
<211> LENGTH: 20
<212> TYPE: DNA
<213> ORGANISM: Artificial
<220> FEATURE:
<221> NAME/KEY: misc_feature
<222> LOCATION: (1)..(20)
<223> OTHER INFORMATION: PCR primer
```

```
<400> SEQUENCE: 12
ttaacttgtt cggccacagc                                                    20

<210> SEQ ID NO 13
<211> LENGTH: 36
<212> TYPE: DNA
<213> ORGANISM: Artificial
<220> FEATURE:
<221> NAME/KEY: misc_feature
<222> LOCATION: (1)..(36)
<223> OTHER INFORMATION: PCR primer

<400> SEQUENCE: 13
ccaaatgaga gatggtaacc ttgaactcta tgagca                                  36

<210> SEQ ID NO 14
<211> LENGTH: 40
<212> TYPE: DNA
<213> ORGANISM: Artificial
<220> FEATURE:
<221> NAME/KEY: misc_feature
<222> LOCATION: (1)..(40)
<223> OTHER INFORMATION: PCR primer

<400> SEQUENCE: 14
gtgctcatag agttcaaggt taccatcttc cctcatttgg                              40

<210> SEQ ID NO 15
<211> LENGTH: 39
<212> TYPE: DNA
<213> ORGANISM: Artificial
<220> FEATURE:
<221> NAME/KEY: misc_feature
<222> LOCATION: (1)..(39)
<223> OTHER INFORMATION: PCR primer

<400> SEQUENCE: 15
ccaaatgagg gaagaaggta taattgaact ctatgagca                               39

<210> SEQ ID NO 16
<211> LENGTH: 40
<212> TYPE: DNA
<213> ORGANISM: Artificial
<220> FEATURE:
<221> NAME/KEY: misc_feature
<222> LOCATION: (1)..(40)
<223> OTHER INFORMATION: PCR primer

<400> SEQUENCE: 16
gtgctcatag agttcaatta taccttcttc cctcatttgg                              40
```